US008404715B2

(12) United States Patent
Rubin

(10) Patent No.: US 8,404,715 B2
(45) Date of Patent: *Mar. 26, 2013

(54) METHODS AND COMPOSITIONS USING RACEMIC, (R)-, AND (S)-FEXOFENADINE IN COMBINATION WITH LEUKOTRIENE INHIBITORS

(75) Inventor: Paul D. Rubin, Sudbury, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/398,669

(22) Filed: Feb. 16, 2012

(65) Prior Publication Data

US 2012/0149730 A1 Jun. 14, 2012

Related U.S. Application Data

(60) Continuation of application No. 10/314,269, filed on Dec. 6, 2002, now abandoned, which is a division of application No. 09/722,395, filed on Nov. 28, 2000, now Pat. No. 6,509,353, which is a division of application No. 09/059,570, filed on Apr. 14, 1998, now Pat. No. 6,194,431.

(51) Int. Cl.
*A61K 31/47* (2006.01)
*A61K 31/445* (2006.01)
*A61K 31/44* (2006.01)
(52) U.S. Cl. ......... 514/314; 514/317; 514/311; 514/301
(58) Field of Classification Search .................. 514/314, 514/317, 311, 301
See application file for complete search history.

(56) References Cited

U.S. PATENT DOCUMENTS

| | | | |
|---|---|---|---|
| 3,878,217 A | 4/1975 | Carr et al. | |
| 4,254,129 A | 3/1981 | Carr et al. | |
| 4,617,407 A | 10/1986 | Young et al. | |
| 4,619,934 A | 10/1986 | Sunshine et al. | |
| 4,742,175 A | 5/1988 | Fawcett et al. | |
| 4,783,465 A | 11/1988 | Sunshine et al. | |
| 4,829,064 A | 5/1989 | Sunshine et al. | |
| 4,929,605 A | 5/1990 | Domet et al. | |
| 4,996,061 A | 2/1991 | Webb et al. | |
| 5,019,591 A | 5/1991 | Gardner et al. | |
| 5,057,427 A | 10/1991 | Wald et al. | |
| 5,077,217 A | 12/1991 | Matson et al. | |
| 5,375,693 A | 12/1994 | Woosley et al. | |
| 5,578,610 A | 11/1996 | D'Ambra | |
| 5,633,272 A | 5/1997 | Talley et al. | |
| 5,900,421 A | 5/1999 | Handley et al. | |
| 5,919,776 A | 7/1999 | Hagmann et al. | |
| 6,054,463 A * | 4/2000 | Handley et al. | 514/290 |
| 6,136,839 A | 10/2000 | Isakson et al. | |
| 6,194,431 B1 | 2/2001 | Rubin | |
| 6,376,528 B1 | 4/2002 | Gregory et al. | |
| 6,509,353 B1 | 1/2003 | Rubin | |

FOREIGN PATENT DOCUMENTS

| | | |
|---|---|---|
| EP | 0 311 067 | 4/1989 |
| EP | 0 815 860 A2 | 1/1998 |
| EP | 0701 443 B1 | 1/1998 |
| FR | 2 453 854 | 11/1980 |
| WO | WO 88/09656 | 12/1988 |
| WO | WO 90/06796 | 6/1990 |
| WO | WO 93/23047 | 11/1993 |
| WO | WO 94/03170 | 2/1994 |
| WO | WO 95/00482 | 1/1995 |
| WO | WO 95/10278 | 1/1995 |
| WO | WO 97/28797 | 8/1997 |
| WO | WO 99/32125 | 7/1999 |

OTHER PUBLICATIONS

Grove, J. Immunology Xii(4) 263-271 (1926).*
Akagi et al., "Inhibitory Effects of Terfenadine on a Variety of Actions Exerted by Leukotriene $D_4$ and Platelet Activating Factor" Oyo Yakuri 35(5):355-371 (1988) with English Abstract.
Akagi et al., 1987, "Antiallergic effects of terfenadine on immediate type hypersensitivity reactions", Immunopharamcol. Immunotoxicol. 9:259-279.
Ariens, 1990, "Stereoselectivity in pharmacodynamics and pharmacokinetics", Schweiz. Med. Wochenschr. 120:131-134.
Ariens, 1990, "Racemische therapeutica probleemmiddelen", Pharmaceutisch Weekblad 125:552-554.
Ariens, 1991, "Racemic therapeutics—ethical and regulatory aspects", Fur. J. Clin. Pharmacol. 41:89-93.
Baroody, F.M., et al., "Effects of Loratadine and Terfenadine on the Induced Nasal Allergic Reaction", Arch. Otolaryngol. Head and Neck Surg., 122:309-316 (1996).
Chan et al.. "Direct Enantiomeric Separation of Terfenadine and Its Major Acid Metabolite by High-Performance Liquid Chromatography, and the Lack of Stereoselective Terfenadine Enantiomer Biotransformation in Man" J. Chromatog. 571:291-297 (1991).
Chan et al., 1990, "Lack of interconversion of the enantiomers of terfenadine in-vivo: the pharmacokinetics and disposition of the individual enantiomers in the male beagle dog", Pharma. Res. 7:S222, abs.PPDM8064.
Chemical Abstracts 112 abstract 171943 (1990).
Chen et al., "Analysis of the Metabolites of Terfenadine in Human Urine by Thermospray Liquid Chromatography—Mass Spectrometry" 3rd International Symposium on Pharmaceutical and Biomedical Analysis (1991).
Chen et al., 1991, "Determination of the metabolites of terfenadine in human urine by thermospray liquid chromatography—mass spectrometry", J. Pharm. Biomed. Anal. 9:929-933.
Cheng et al., "Antihistaminic Effect of Terfenadine: A New Piperidine-type Antihistamine" Drug Dev. Res. 2:181-196 (1982).
Cohen et al., "Meclizine and Placebo in Treating Vertigo of Vestubular Origin, Relative Efficacy in a Double-Blind Study" Arch. Neurol. 27:129-135 (1972).
Connell, J.T.. "Pharmacology and Clinical Efficacy of Terfenadine, a New $H_1$ -Receptor Antagonist" Pharmacotherapy 5(4):201-208 (1985).

(Continued)

*Primary Examiner* — Shirley V Gembeh
(74) *Attorney, Agent, or Firm* — Jones Day

(57) ABSTRACT

Methods and pharmaceutical compositions employing a terfenadine metabolite and a leukotriene inhibitor for the treatment or prevention of inflammation or allergic disorders, such as asthma, or symptoms thereof. Also included are methods and compositions employing a terfenadine metabolite, a leukotriene inhibitor, and a decongestant for the treatment or prevention of inflammation or allergic disorders, such as asthma, or symptoms thereof.

15 Claims, No Drawings

OTHER PUBLICATIONS

Coutant et al., 1991, "Determination of terfenadine and terfenadine acid metabolite in plasma using solid-phase extraction and high-performance liquid chromatography with fluorescence detection", J. Chromatography 570:139-148.

F-D-C Reports, "Trade and Govt. Memos", Feb. 9. 1998.

Garteiz et al., "Pharmacokinetics and Biotransformation Studies of Terfenadine in Man" Arzneim.-Forsch./Drug Res. 32(II):1185-1190 (1982).

Honig et al., 1992, "Changes in the pharmacokinetics and electrocardiographic pharmacodynamics of terfenadine with concomitant administration of erythromycin", Clin. Pharma. Ther. 52:231-238.

Knowles, S., The Canadian Journal of Hospital Pharmacy, 45:33 (1992).

Ku, Y., et al.. "Effects of Histamine $H_1$ Receptor Antagonists on Action Potentialists in Guinea-Pig Isolated Papillary Muscles", Arch. Int. Pharmacodyn., 331:59-73 (1996).

Merck Index, "6340, Montelukast," p. 1070, Twelfth Edition (1996).

Miadonna et al., 1994, "Inhibitory Effect of the H1 Antagonist Loratadine on Histamine Release from Human Basophils", Int. Arch. Allergy Immunol. 105:12-17.

Monahan et al., "Torsades de Pointes Occurring in Association With Terfenadine Use" JAMA 264(2):2788-2790 (1990).

Okerholm et al., "Bioavailability of Terfenadine in Man" Biopharm. Drug Dispos. 2:185-190 (1981).

Physician's Desk Reference. pp. 303, 474-476, 3148-3149 (1988).

Physician's Desk Reference, pp. 1349-1350 (1992).

Printed product information of Jul. 1990 for Seldane distributed by Marion Merrell Dow Inc.

Rampe et al., Molecular Pharmacology, 44: 1240-1245 (1993).

Roquet. A., et al., "Combined Antagonism of Leukotriene and Histamine Produces Predominant Inhibition of Allergen-Induced Early and Late Phase Airway Obstruction in Asthmatics", Am. J. Respir. Crit. Care Med., 155:1856-1863 (1997).

Satoskar, R.S. et al., "Anti-Histaminic Agents," Pharmacology & Pharmacotherapy, Moscow:Meditsina, 320-325(1986).

Suttle et al., "The Pharmacokinetics of Zafirlukast and Terfenadine After Coadministration to Healthy Men", Allergy, 52(S37):184 (1997).

Tasaka et al., 1986. "Intracellular calcium release induced by histamine releasers and its inhibition by some antiallergic drugs", Ann. Allergy 56:464-469.

Tasaka et al., 1988, "Antiallergic effects of terfenadine on immediate type hypersensitivity reactions and the mechanisms of those actions", Yakuri to Chiryo 16:2465-2480.

Temple et al., 1988, "Loratadine, an Antihistamine, Blocks antigen- and Ionophore-Induced Leukotriene Release From Human Lung In Vitro", Prostaglandins 35(4):549-554.

Testa et al., 1990, "Racemates verses enantiomers in drug development: dogmatism or pragmatism?", Chirality 2:129-133.

Warning Letter of Aug. 6, 1990, distributed to U.S. Physicians by Marion Merrell Dow Inc. on or about that date.

Wood, C.D., "Antimotion Sickness and Antiemetic Drugs" Drugs 17:471-479 (1979).

Woosley et al., 1993, "Mechanism of the cardiotoxic actions of terfenadine", JAMA 269:1532-1536.

Yuan et al., J. of Allergy and Clinical Immun., vol. 85, No. 5, 1990, pp. 865-871.

Zamani et al., 1991, "Enantiomeric analysis of terfenadine in rat plasma by HPLC", Chirality 3:467-470.

Zhang, M.Q., & Timmerman, H., "Leukotriene $cysLT_1$ ($LTD_4$) receptor antagonism of $H_1$ —antihistamines: An in vitro study", Intlamm. Res., 46(1):S93-S94 (1997).

Hjorth, "Terfenadine in the Treatment of Chronic Idiopathic Urticaria and Atopic Dermatitis", Cutis: Cutaneous Medicine for the Practitioner 42(A):29-30 (1988).

Yamamoto et al., "Anti-inflammatory Action of Orally Active 5-Lipoxygenase Inhibitor TMK688", Pharmacology 48(5):273-282 (1994).

Fretland et al., "Antiintlammatory Effects of Second-Generation Leukotriene B4 Receptor Antagonist, SC-53228", Inflammation 19(2):193-205 (1995).

"Seborrheic Dermatitis", American Academy of Dermatology, 2003, http://www.aad.org/public/Publications/pamphlets/SeborrheicDermatitis.htm.

Markham et al., "Fexofenadine", Drugs 55(2): 269-274 (1998) (abstract only).

Fireman et al., "Treatment Strategies Designed to Minimize Medical Complications of Allergic Rhinitis", Am. J. Rhinology 11(2):95-102 (1997) (abstract only).

Harris et al., "Clinical Activity of Leukotriene Inhibitors", Int. J. Immunopharmacology 17(2):147-156 (1995).

Grove, "Studies in Specific Hypersensitiveness XXVI. On Asthma and Dermatitis due to Hypersensitiveness to Pediculoides Ventricosus", J. Immunology XII(4):263-271 (1926).

Online Health Dictionary: wheals (Sep. 1. 2008), http://www.123exp-health.com/t/OI081102894/.

* cited by examiner

METHODS AND COMPOSITIONS USING RACEMIC, (R)-, AND (S)-FEXOFENADINE IN COMBINATION WITH LEUKOTRIENE INHIBITORS

This application is a continuation application of U.S. application Ser. No. 10/314,269, filed Dec. 6, 2002 now abandoned, which is a divisional application of U.S. application Ser. No. 09/722,395, filed Nov. 28, 2000, now U.S. Pat. No. 6,509,353, which is a divisional application of U.S. application Ser. No. 09/059,570, filed Apr. 14, 1998, now U.S. Pat. No. 6,194,431, the entireties of which are incorporated herein by reference.

1. FIELD OF THE INVENTION

The invention relates to methods of treating asthma, allergic conditions, and inflammation. In another aspect, this invention relates to the use of antihistamines and leukotriene inhibitors, and to compositions containing them.

2. BACKGROUND OF THE INVENTION

Terfenadine is an antagonist of the H-1 histamine receptor protein, which mediates the response antagonized by conventional antihistamines. Terfenadine is well absorbed but is extensively metabolized. See Okerholm et al., *Biopharmaceutics and Drug Distribution*, 2: 185-190 (1981). Two main metabolites have been identified and one of the metabolites, fexofenadine, chemically named 4-[1-hydroxy-4-[4-(hydroxydiphenylmethyl-1-piperidinyl)butyl]-α,α-dimethylbenzeneacetic acid, is reported to have antihistaminic activity. See Gartiez et al., *Arzneimittel Forschung/Drug-Research;* 32: 1185-1190 (1982).

Recently, the FDA has approved the use of fexofenadine as a prescription antihistamine (ALLEGRA®) for allergic rhinitis. Fexofenadine is said to have the beneficial effects of terfenadine while having a reduced risk of cardiotoxicity. See, e.g., U.S. Pat. No. 5,375,683.

It has been suggested that the moderate effectiveness of some $H_1$-antihistamines are due to their additional activity against leukotrienes, particularly $LTD_4$. In one study of guinea pigs, the increase in airway resistance caused by $LTD_4$ (leukotriene $D_4$ was suppressed by terfenadine. See Akagi et al., *Oyo Yakuri*, 35: 361-371 (1988). Another study was conducted that investigated the development of dual antagonists of $H_1$- and $LTD_4$-receptors. Twenty (20) $H_1$-antihistamines with diverse chemical structures were tested for activity against $LTD_4$-induced contraction in isolated guinea-pig ileum and displacement of [$^3$H]$LTD_4$ from guinea-pig lung membrane proteins [M. Zhang et al., *Inflamm. res.* 46:Supp. I S93-S94 (1997)]. The results indicated the drugs were weakly active in inhibiting $LTD_4$-induced contraction of guinea pig ileum. The study further mentioned a possible mechanism for loratadine and terfenadine, but concluded that the mechanism does not appear to warrant great attention for drug development.

Similarly, F. Baroody et al. report that terfenadine treatment partially inhibits the early nasal response to allergen challenge and subsequent reactivity to a challenge with methacholine without affecting the influx of eosinophils into nasal secretions. Treatment tended to decrease levels of tryptase, prostaglandin $D_2$ and leukotriene $C_4$, but the differences did not achieve statistical significance relative to the placebo [F. Baroody et al., *Arch. Otolaryngol. Head Neck Surg.*, 122:309-316 (March 1996)].

Compounds within the class of non-sedating antihistamines have been known to cause severe adverse electrophysiologic side-effects when administered to a human. These adverse side-effects are associated with a prolonged QT interval and include, but are not limited to, ventricular fibrillation and cardiac arrhythmias, such as ventricular tachyarrhythmias or torsades de pointes. Quercia et al., *Hosp. Formul.* 28: 137, 142 (1993); Knowles, *Canadian Journal Hosp. Pharm.*, 45: 33,37 (1992); Craft, *British Medical Journal*, 292: 660 (1986); Simons et al., *Lancet*, 2: 624 (1988); and Unknown, *Side Effects of Drugs Annual*, 12: 142 and 14: 135. More recently, clinical practitioners have noted an increase in the occurrence of these cardiac arrhythmias upon co-administration of terfenadine with other drugs such as ketoconazole and erythromycin or upon overdose of terfenadine. Quercia et al., *Hosp. Formul.* 28: 137, 142 (1993).

Leukotrienes augment neutrophil and eosinophil migration, neutrophil and monocyte aggregation, leukocyte adhesion, increase capillary permeability, and smooth muscle contraction, all of which contribute to inflammation, edema, mucus secretion, and bronchoconstriction. For example, zileuton, commercially available as ZYFLO®, is a specific inhibitor of 5-lipoxygenase and has the chemical name (±)-1-(1-Benso[b]thien-2-ylethyl)-1-hydroxyurea. Zileuton is known to inhibit leukotriene ($LTH_4$, $LTC_4$, $LTD_4$, and $LTE_4$) formation in vitro. Zileuton is an inhibitor ex vivo of $LTB_4$ formation in several species and inhibits leukotriene-dependent smooth muscle contractions in vitro in guinea pig and human airways. One study of 373 patients indicated that 600 mg of zileuton four times daily were required to provide efficacy, while 400 mg failed to do so. In some patients, zileuton was reported to cause headache, pain, asthenia, dyspepsia, nausea, and myalgia. [Physician's Desk Reference, 52 ed., Medical Economics Co., Inc., 474-76 (1998)].

Zafirlukast, sold commercially as ACCOLATE®, is another type of leukotriene inhibitor. This leukotriene inhibitor is a leukotriene receptor antagonist (LTRA) of leukotriene $D_4$ and $E_4$, and has the chemical name 4-(5-cyclopentyloxycarbonylamino-1-methyl-indol-8-ylmethyl)-3-methoxy-N-o-tolylsulfonylbenzamide. Cysteinyl leukotriene production and receptor occupation have been correlated with the pathophysiology of asthma. In vitro studies indicated that zafirlukast antagonized the contractile activity of three leukotrienes in conducting airway smooth muscle from laboratory animals and humans; prevented intradermal $LTD_4$-induced increases in cutaneous vascular permeability; and inhibited inhaled $LTD_4$-induced influx of eosinophils into animal lungs. In some patients, zafirlukast has been reported to cause headache, infection, nausea, diarrhea, pain, asthenia, abdominal pain, dizziness, myalgia, fever, vomiting, SGPT elevation, and dyspepsia. [Physician's Desk Reference, 52 ed., Medical Economics Co., Inc., 3148-49 (1998)].

3. SUMMARY OF THE INVENTION

The present invention represents an improvement over terfenadine and the terfenadine metabolites, as well as the leukotriene inhibitor, technology presently available.

This invention relates to novel pharmaceutical compositions comprising: (a) a metabolite of terfenadine; (b) a leukotriene inhibitor; and optionally (c) a decongestant; and a pharmaceutically acceptable carrier or excipient. A "metabolite of terfenadine" or a "terfenadine metabolite," as defined herein, includes 4-[1-hydroxy-4-(4-hydroxydiphenylmethyl-1-piperidinyl)butyl]-α,α-dimethylbenzeneacetates, 4-[1-hydroxy-4-(4-hydroxydiphenylmethyl-1-piperidinyl)butyl-α, α-dimethylbenzeneacetic acid (fexofenadine), and 1-[p-(2- hydroxymethyl-2-propyl)phenyl)-4-[4-(α-hydroxy-α-phenylbenzyl)-1-piperidinyl]butanol, or an optically pure stereoisomer of any of the above compounds, or a pharmaceutically acceptable salt of any of the above compounds or stereoisomers (See, e.g., U.S. Pat. No. 5,375,683).

The compositions of the invention employing a terfenadine metabolite and a leukotriene inhibitor, and optionally a decongestant, possess potent antihistaminic activity and are useful in treating, preventing, or managing asthma, asthma symptoms, allergic rhinitis, inflammation, and other allergic disorders, as well as dermatitis. The compositions employing a terfenadine metabolite and a leukotriene inhibitor are preferred, and these provide an improvement in overall therapy relative to terfenadine or a terfenadine metabolite alone. In addition, the compositions of the invention reduce or avoid adverse effects associated with administration of other non-sedating antihistamines or derivatives thereof, such as terfenadine, including, but not limited to, cardiac arrhythmias, drowsiness, nausea, fatigue, weakness and headache. The compositions of a terfenadine metabolite and a leukotriene inhibitor are also useful in combination with non-steroidal anti-inflammatory agents or other non-narcotic analgesics for the treatment or prevention of cough, cold, cold-like, and/or flu symptoms and the discomfort, headache, pain, fever, and general malaise associated therewith. The aforementioned combinations (e.g., a terfenadine metabolite and a leukotriene inhibitor) may optionally include one or more other active components including a decongestant, cough suppressant/antitussive, or expectorant.

Additionally, the novel pharmaceutical compositions of the invention are useful in treating, preventing, or managing motion sickness, vertigo, diabetic retinopathy, small vessel complications due to diabetes and such other conditions as may be related to the activity of these derivatives as antagonists of the H-1 histamine receptor. The compositions can be used to treat or prevent these disorders while reducing or avoiding adverse effects associated with administration of other non-sedating antihistamines including α-aryl-4-substituted piperidinoalkanol derivatives, such as terfenadine.

In one embodiment, this invention provides for a method of preventing or treating asthma or asthma symptoms in a human which comprises administering to a human a therapeutically effective amount of a terfenadine metabolite and a therapeutically effective amount of a leukotriene inhibitor.

The invention also provides a method of preventing or treating asthma or asthma symptoms in a human, comprising administering to a human a composition, said composition comprising (i) a therapeutically effective amount of a terfenadine metabolite or a pharmaceutically acceptable salt thereof; (ii) a leukotriene inhibitor selected from the group consisting of 5-lipoxygenase inhibitors, 5-lipoxygenase activating protein antagonists, and leukotriene receptor antagonists; (iii) optionally a therapeutically effective amount of a decongestant; and a pharmaceutically acceptable carrier or excipient.

This invention is further directed to a method of preventing or treating asthma or the symptoms of asthma in a human which comprises administering to a human therapeutically effective amounts of a terfenadine metabolite, a leukotriene inhibitor, and a decongestant.

In a second embodiment, the invention also provides for a method of preventing or treating allergic rhinitis in a human which comprises administering to a human a therapeutically effective amount of a terfenadine metabolite, or a pharmaceutically acceptable salt thereof, a leukotriene inhibitor, and optionally a decongestant, such that all three active ingredients are used.

In a third embodiment, the invention provides for a method of preventing or treating dermatitis in a human which comprises administering to a human a therapeutically effective amount of a terfenadine metabolite or a pharmaceutically acceptable salt thereof, a leukotriene inhibitor, and optionally a decongestant, such that all three active ingredients are used.

In a fourth embodiment, the invention provides for a method of preventing or treating inflammation in a human which comprises administering to a human a therapeutically effective amount of a terfenadine metabolite or a pharmaceutically acceptable salt thereof, a leukotriene inhibitor, and optionally a decongestant, such that all three active ingredients are used.

In a fifth embodiment, the invention provides for a method of preventing or treating a condition responsive to leuktotriene inhibition in a human which comprises administering to a human a therapeutically effective amount of a terfenadine metabolite or a pharmaceutically acceptable salt thereof, a leukotriene inhibitor, and optionally a decongestant, such that all three active ingredients are used.

It should be recognized that the compositions and methods include the use of optically pure stereoisomers of the terfenadine metabolites, as well as pharmaceutically acceptable salts of the stereoisomers. Thus, the invention includes the (R)- and (S)-enantiomer, and the racemic mixture, or a pharmaceutically acceptable salt thereof, of each terfenadine metabolite. The methods and compositions preferably employ racemic fexofenadine, or optically pure (R)-fexofenadine or (S)-fexofenadine, or pharmaceutically acceptable salts thereof, more preferably (R)-fexofenadine substantially free of (S)-fexofenadine or (S)-fexofenadine substantially free of (R)-fexofenadine, or pharmaceutically acceptable salts thereof.

The invention encompasses the treatment, prevention, and/or management of asthma, the symptoms of asthma, dermatitis, allergic rhinitis, or inflammation using a metabolite of terfenadine, preferably fexofenadine, and a leukotriene inhibitor. The invention also encompasses the treatment, prevention, and/or management of these disorders with a terfenadine metabolite, a leukotriene inhibitor, and optionally a decongestant. The invention encompasses the treatment, prevention, and/or management of these disorders using a single unit dosage form that contains a terfenadine metabolite, a leukotriene inhibitor and optionally a decongestant, such that a terfenadine metabolite and a leukotriene inhibitor or all three active ingredients are used. However, it should be recognized that combination therapy by separate administration of each active ingredient is also contemplated. The methods and compositions of this invention are believed to reduce or avoid adverse effects associated with the administration of non-sedating antihistamines, such as terfenadine. The methods and compositions described herein are believed to provide superior or improved therapy over prior art methods and compositions involving a terfenadine metabolite in the absence of a leukotriene inhibitor, or a leukotriene inhibitor in the absence of a terfenadine metabolite. Without being limited by theory, it is believed that the combination of a terfenadine metabolite, a leukotriene inhibitor, and optionally a decongestant, provides superior, improved, and synergistic effects unachievable by any of these compounds alone.

4. DETAILED DESCRIPTION OF THE INVENTION

The administration of a terfenadine metabolite, a leukotriene inhibitor, and optionally a decongestant, in the methods of the present invention may be either concurrently or sequentially, i.e., a terfenadine metabolite, a leukotriene inhibitor, and the optional decongestant may be administered as a combination (a single unit dosage) or concurrently but separately. They may also be provided by the sequential administration of a terfenadine metabolite, leukotriene inhibitor, and the optional decongestant, by sequential administration of a terfenadine metabolite, decongestant, and leukotriene inhibitor, by sequential administration of leukotriene inhibitor, a terfenadine metabolite, and decongestant, or in any other possible order, such as decongestant followed by concurrent administration of a terfenadine metabolite and leukotriene inhibitor. The compositions administered in each of these methods may be concurrent, sequential, or in any combination of concurrent and/or sequential.

Adverse effects to be reduced or avoided by the methods and compositions of the present invention include, but are not limited to: cardiotoxicity, such as cardiac arrhythmia or cardiac conduction disturbances; drowsiness; nausea; fatigue; weakness; and headache.

Terfenadine metabolites and the isomers and salts thereof, particularly fexofenadine and the isomers and salts thereof, and other non-sedating antihistamines have antihistaminic activity and provide therapy and a reduction of symptoms for a variety of conditions and disorders related to allergic rhinitis and other allergic disorders, diabetes mellitus, and other conditions; however, such drugs, while offering the expectation of efficacy, may cause adverse effects. Utilizing a metabolite of terfenadine, preferably fexofenadine, in combination with a leukotriene inhibitor, and optionally with a decongestant, results in clearer dose-related definitions of efficacy, diminished adverse effects, a superior therapy due to synergistic activity, and accordingly, an improved therapeutic index. It is, therefore, more desirable to use the compositions and methods of the invention than to use terfenadine, or a metabolite thereof, or a leukotriene inhibitor separately.

One of ordinary skill in the art is readily able to synthesize fexofenadine or the other metabolites of terfenadine, as well as their optically pure stereoisomers and salts thereof, used in the compositions and methods of the invention, such as by following the teachings of U.S. Pat. Nos. 4,254,129; 5,578,610; 5,581,011; 5,589,487; and 5,663,412, the disclosures of which are hereby expressly incorporated herein by reference thereto.

The term "adverse effects" as used herein includes, but is not limited to, cardiac arrhythmias, cardiac conduction disturbances, appetite stimulation, weight gain, sedation, gastrointestinal distress, headache, dry mouth, constipation, and diarrhea. The term "cardiac arrhythmias" includes, but is not limited to, ventricular tachyarrhythmias, torsades de pointes, and ventricular fibrillation.

The phrase "therapeutically effective amount" as used herein means the amount of a terfenadine metabolite that provides a therapeutic benefit in the treatment, prevention, or management of conditions that are responsive to histamine antagonists, such as urticaria, allergic rhinitis, inflammation, symptomatic dermographism, dermatitis, asthma, allergic asthma, retinopathy or other small vessel disorders associated with diabetes mellitus, and the symptoms associated with asthma or allergic rhinitis such as bronchoconstriction, cough, cold, cold-like, wheezing, dyspnea, and/or flu symptoms including, but not limited to, sneezing, rhinorrhea, lacrimation, and dermal irritation.

The phrase "therapeutically effective amount" as used herein means the amount of leukotriene inhibitor that provides a therapeutic benefit in the treatment, prevention, or management of conditions that are responsive to leukotriene inhibitors, such as urticaria, allergic rhinitis, symptomatic dermographism, dermatitis, asthma, inflammation, retinopathy or other small vessel disorders associated with diabetes mellitus, and the symptoms associated with asthma and allergic rhinitis such as bronchoconstriction, cough, cold, cold-like, wheezing, dyspnea, and/or flu symptoms including, but not limited to, sneezing, rhinorrhea, lacrimation, and dermal irritation.

The phrase "therapeutically effective amount" with respect to decongestant as used herein means that amount of decongestant alone, or in combination with other drugs, that provides a therapeutic benefit in the treatment, prevention, or management of any condition that is responsive to decongestants, such as congestion of the respiratory tract and/or the sinuses, and the symptoms associated with congestion, such as cough, cold, cold-like, wheezing, dyspnea, and/or flu symptoms including, but not limited to, sneezing, rhinorrhea, lacrimation, and dermal irritation.

The term "asthma" as used herein is defined as a disorder characterized by increased responsiveness of the trachea and bronchi to various stimuli, which results in symptoms that include, but are not limited to, wheezing, cough, shortness of breath, bronchoconstriction, dyspnea, and the like. Asthma includes, for example, allergic asthma.

The term "dermatitis" as used herein means that disorder caused by inflammation to the skin including endogenous and contact dermatitis such as, but not limited to: actinic dermatitis (or photodermatitis), atopic dermatitis, chemical dermatitis, cosmetic dermatitis, dermatitis aestivalis, and seborrheic dermatitis.

The term "inflammation" as used herein is a fundamental pathologic process of a dynamic complex of cytologic and chemical reactions that occur in the affected blood vessels and adjacent tissues in response to an injury or abnormal stimulation caused by a physical, chemical, or biologic agent, including: the local reactions and resulting morphologic changes; the destruction or removal of the injurious material; and the responses that lead to repair and healing. The typical signs of inflammation are redness, heat or warmth, swelling, pain, and occasionally inhibited or lost function. All of the signs may be observed in certain instances, although any particular sign is not necessarily always present.

The term "leukotriene inhibitor" as used herein includes any agent or compound that inhibits, restrains, retards or otherwise interacts with the action or activity of leukotrienes, such as, but not limited to, 5-lipoxygenase ("5-LO") inhibitors, 5-lipoxygenase activating protein ("FLAP") antagonists, and leukotriene receptor antagonists ("LTRAs"), including leukotriene receptor antagonists ("LTRAs"). An exemplary LTRA is leukotriene $D_4$ ("$LTD_4$") receptor antagonist.

The term "5-lipoxygenase inhibitor" or "5-LO inhibitor" as used herein includes any agent or compound that inhibits, restrains, retards or otherwise interacts with the enzymatic action of 5-lipoxygenase, such as, but not limited to, zileuton, docebenone, piripost, and ICI-D2318.

The term "5-lipoxygenase activating protein antagonist" or "FLAP antagonist" as used herein includes any agent or compound that inhibits, restrains, retards or otherwise interacts with the action or activity of 5-lipoxygenase activating protein, such as, but not limited to, MK-591 and MK-886.

The term "leukotriene receptor antagonist" or "LTRA" as used herein includes any agent or compound that inhibits, restrains, retards or otherwise antagonizes the activity of receptors that are responsive to leukotrienes, including those responsive to leukotriene $D_4$. Exemplary LTRAs include, but are not limited to, sodium 1-(((R)-(3-(2-(6,7-difluoro-2-quinolinyl)ethynyl)phenyl)-3-(2-(2-hydroxy-2-propyl)phenyl)thio)methyl)cyclopropaneacetate; 1-(((1(R)-(3-(2-(2,3- dichlorothieno[3,2-b]pyridin-5-yl)-(E)-ethenyl)phenyl)-3-(2-(1-hydroxy-1-methylethyl)phenyl)propyl)thio)methyl) cyclopropaneacetic acid or sodium or other salts thereof, pranlukast, zafirlukast (ICI-204219), and montelukast (MK-476), the latter of which is sold commercially as SINGULAIR®.

The magnitude of a prophylactic or therapeutic dose of a terfenadine metabolite or leukotriene inhibitor in the acute or chronic management of a disorder or condition will vary with the severity of the condition to be treated and the route of administration. The dose, and perhaps the dose frequency, will also vary according to the age, body weight, and response of the individual patient. Suitable total daily dose ranges can be readily determined by those skilled in the art. In general, the total daily dose range for a terfenadine metabolite, for the conditions described herein, is from about 0.01 mg to about 500 mg administered in single or divided doses. For example, a preferred oral daily dose range should be from about 1 mg to about 500 mg. A more preferred oral dose is about 20 mg to about 200 mg. A preferred oral daily dose range of decongestant, such as pseudoephedrine, should be from about 50 mg to about 300 mg, more preferably, about 150 mg to about 250 mg. In addition, suitable oral daily dosage ranges of leukotriene inhibitor can be readily determined by those skilled in the art. For example, see the Physician's Desk Reference® 1998 for suitable dosages presently used for known leukotriene inhibitors. For example, for 5-lipoxygenase inhibitors, the oral daily dose range should be from about 20 mg to 2,500 mg, preferably from about 20 mg to 800 mg. For leukotriene receptor antagonists, the oral daily dose range should be from about 2 mg to 100 mg, preferably from about 5 mg to 20 mg.

It is further recommended that children, patients aged over 65 years, and those with impaired renal or hepatic function initially receive low doses, and that they then be titrated based on individual response(s) or blood level(s). It may be necessary to use dosages outside these ranges in some cases as will be apparent to those skilled in the art. Further, it is noted that the clinician or treating physician will know how and when to adjust, interrupt, or terminate therapy in conjunction with individual patient response.

The term "therapeutically effective amount of a terfenadine metabolite or a pharmaceutically acceptable salt thereof" is encompassed by the above-described dosage amounts. In addition, the terms "said composition comprising (i) a therapeutically effective amount of a terfenadine metabolite or a pharmaceutically acceptable salt thereof; and (ii) a therapeutically effective amount of a leukotriene inhibitor" and "said composition comprising (i) a therapeutically effective amount of a terfenadine metabolite or a pharmaceutically acceptable salt thereof; (ii) a therapeutically effective amount of a leukotriene inhibitor; and (iii) a therapeutically effective amount of a decongestant" are also encompassed by the above-described dosage amounts and dose frequency schedule.

Any suitable route of administration may be employed for providing the patient with an effective dosage of a terfenadine metabolite and leukotriene inhibitor according to the methods of the present invention. For example, oral, intraoral, rectal, parenteral, epicutaneous, transdermal, subcutaneous, intramuscular, intranasal, sublingual, buccal, intradural, intraocular, intrarespiratory, or nasal inhalation and like forms of administration may be employed. Oral administration is generally preferred. For the methods to treat dermatitis, however, topical administration is preferred.

The pharmaceutical compositions used in the methods of the present invention, which are sterile and stable, include a terfenadine metabolite, the metabolic derivative of terfenadine, or a pharmaceutically acceptable salt thereof, a leukotriene inhibitor, and optionally a decongestant, as the active ingredient. The compositions may also contain a pharmaceutically acceptable carrier or excipient, and optionally, other therapeutic ingredients.

The term "pharmaceutically acceptable salt" refers to a salt prepared from pharmaceutically acceptable non-toxic acids or bases including inorganic acids or bases or organic acids or bases. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), lysine and procaine.

The compositions for use in the methods of the present invention can include suitable excipients or carriers such as starches, sugars, microcrystalline cellulose, diluents, granulating agents, lubricants, binders, disintegrating agents, and the like.

Dosage forms include tablets, troches, dispersions, suspensions, solutions, capsules, patches, gel caps, syrups, elixirs, gels, powders, magmas, lozenges, ointments, creams, pastes, plasters, lotions, discs, suppositories, nasal or oral sprays, aerosols, and the like.

Because of their ease of administration, tablets and capsules represent the most advantageous oral dosage unit form, in which case solid pharmaceutical carriers are employed. If desired, tablets may be coated by standard aqueous or non-aqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are expressly incorporated herein by reference thereto.

Pharmaceutical compositions for use in the methods of the present invention may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

The invention is further defined by reference to the following example describing in detail the preparation of the composition and the compositions used in the methods of the present invention, as well as their utility. It will be apparent to those skilled in the art that many modifications, both to materials and methods, may be practiced which are within the scope of this invention.

5. EXAMPLES

5.1. Example 1

A. Preparation of Methyl R-4-(1-hydroxy-4-(4-hydroxydiphenylmethyl-1-piperidinyl)butyl)-α,α-dimethylbenzeneacetate 4-(α-hydroxy-α-phenylbenzyl)piperidine (4.3 g) was combined with methyl p-(4-chloro-1-oxobutyl)-α,α-dimethylbenzeneacetate (4.5 g), potassium bicarbonate (2.9 g), potassium iodide (ca. 50 mg), and methyl isobutyl ketone (50 mL) and heated to reflux for 48 hrs. Additional 4-(α-hydroxy-α-phenylbenzyl)piperidine (1.1 g) was added, and heating was continued for an additional 48 hrs. Upon cooling the mixture to room temperature, water was added and the pH of the solution was adjusted to ca. 12 by addition of aqueous sodium hydroxide. The mixture was extracted with ethyl acetate. The ethyl acetate solution was washed with saturated aqueous sodium bicarbonate and brine and dried over sodium sulfate. The ethyl acetate was removed on a rotary evaporator and the residue was treated with 25% ethyl acetate in hexane. The resulting precipitate was filtered and air dried to give methyl 4-[1-oxo-4-(4-hydroxydiphenylmethyl-1-piperidinyl)butyl]-α,α-dimethylbenzeneacetate. This intermediate precipitate (2.4 g) was combined with tetrahydrofuran (10 mL) and (+)-β-chlorodiisopinocamphenylborane (4.5 g) and stirred for 48 hrs. Methanol (10 mL and sodium bicarbonate (1.5 g) were added to the reaction solution, and the mixture was stirred for 12 hrs. The mixture was diluted with ethyl acetate (200 mL) and washed with saturated aqueous sodium bicarbonate to give methyl R-4-[1-hydroxy-4-(4-hydroxydiphenylmethyl-1-piperidinyl)butyl]-α,α-dimethylbenzeneacetate.

B. R-(+)-4-[1-hydroxy-4-(4-hydroxydiphenylmethyl-1-piperidinyl)butyl]-α,α-dimethylbenzeneacetic acid [R-(+)-terfenadine Carboxylate]

Methyl R-4-[1-hydroxy-4-(4-hydroxydiphenylmethyl-1-piperidinyl)butyl]-α,α-dimethylbenzeneacetate (1.2 g) was combined with potassium hydroxide (0.4 g) and ethanol (5 mL), and the mixture was heated to reflux for 7 hours. The ethanol was removed on a rotary evaporator and the residue was dissolved in water (2 mL). The aqueous solution was acidified with glacial acetic acid to provide a solid which was recrystallized two times from 1:1 methanol/ethyl acetate to give R-4-[1-hydroxy-4-(4-hydroxydiphenylmethyl-1-piperidinyl)butyl]-α,α-dimethylbenzeneacetic acid (R-terfenadine carboxylate) (mp=213-215° C.).

C. Preparation of Methyl S-4-[1-hydroxy-4-(4-hydroxydiphenylmethyl-1-piperidinyl)butyl]-α,α-dimethylbenzeneacetate 4-(α-hydroxy-α-phenylbenzyl)piperidine (4.3 g) was combined with methyl p-(4-chloro-1-oxobutyl)-α,α-dimethyl-benzene-acetate (4.5 g), potassium bicarbonate (2.9 g), potassium iodide (ca. 50 mg), and methyl isobutyl ketone (50 mL) and heated to reflux for 48 hours. Additional 4-(α-hydroxy-α-phenylbenzyl)piperidine (1.1 g) was added, and heating was continued for an additional 48 hours. Upon cooling the mixture to room temperature, water was added and the pH of the solution was adjusted to ca. 12 by addition of aqueous sodium hydroxide. The mixture was extracted with ethyl acetate. The ethyl acetate solution was washed with saturated aqueous sodium bicarbonate and brine and dried over sodium sulfate. The ethyl acetate was removed on a rotary evaporator and the residue was treated with 25% ethyl acetate in hexane. The resulting precipitate was filtered and air dried to give methyl 4-[1-oxo-4-(4-hydroxydiphenyl-methyl-1-piperidinyl)butyl]-α,α-dimethylbenzeneacetate. This intermediate precipitate (2.4 g) was combined with tetrahydrofuran (10 mL) and (−)-β-chlorodiisopinocamphenylborane (4.5 g) and stirred for 48 hours. Methanol (10 mL) and sodium bicarbonate (1.5 g) were added to the reaction solution and the mixture was stirred for 12 hours. The mixture was diluted with ethyl acetate (200 mL) and washed with saturated aqueous sodium bicarbonate to give methyl S-4-[1-hydroxy-4-(4-hydroxydiphenylmethyl-1-piperidinyl)butyl]-α,α-dimethylbenzeneacetate. If the aforementioned intermediate precipitate was to be reacted with racemic β-chlorodiisopinocamphenylborane, then a racemic mixture of methyl 4-[1-hydroxy-4-(4-hydroxydiphenylmethyl-1-piperidinyl)butyl]-α,α-dimethylbenzeneacetate would be produced.

D. S-(−)-4-[1-hydroxy-4-(4-hydroxydiphenylmethyl-1-piperidinyl)butyl]-α,α-dimethylbenzeneacetic acid [S-(−)-terfenadine Carboxylate]

Methyl S-4-[1-hydroxy-4-(4-hydroxydiphenylmethyl-1-piperidinyl)butyl]-α,α-dimethylbenzeneacetate (1.2 g) was combined with potassium hydroxide (0.4 g) and ethanol (5 mL) and the mixture was heated to reflux for 7 hours. The ethanol was removed on a rotary evaporator and the residue was dissolved in water (2 mL). The aqueous solution was acidified with glacial acetic acid to provide a solid which was recrystallized two times from 1:1 methanol/ethyl acetate to give S-(−)-4-[1-hydroxy-4-(4-hydroxydiphenylmethyl-1-piperidinyl)butyl]-α,α-dimethylbenzeneacetic acid [(S)-terfenadine carboxylate] (mp=215-218° C.).

Various modifications of the invention in addition to those shown and described herein will be apparent to those skilled in the art from the foregoing description. Such modifications are also intended to fall within the scope of the appended claims.

The above disclosure includes all the information deemed essential to enable those skilled in the art to practice the claimed invention. Because the cited patents or publications may provide further useful information these cited materials are incorporated herein in their entireties by reference thereto.

What is claimed is:

1. A method of treating dermatitis in a human which comprises administering to the human a therapeutically effective amount of racemic fexofenadine, (R)-fexofenadine, (S)-fexofenadine, or a pharmaceutically acceptable salt thereof, and a therapeutically effective amount of zileuton, docebenone, piripost, ICI-D2318, or a pharmaceutically acceptable salt thereof.

2. The method of claim 1, wherein the amount of racemic fexofenadine, (R)-fexofenadine, (S)-fexofenadine, or a pharmaceutically acceptable salt thereof, is from 0.01 to 500 mg.

3. The method of claim 1, wherein the amount of the zileuton, docebenone, piripost, or ICI-D2318, or a pharmaceutically acceptable salt thereof, is from 20 mg to 2500 mg.

4. The method of claim 1, wherein optically pure (R)-fexofenadine, or a pharmaceutically acceptable salt thereof, is administered.

5. The method of claim 1, wherein optically pure (S)-fexofenadine, or a pharmaceutically acceptable salt thereof, is administered.

6. A method of treating dermatitis in a human which comprises administering to the human a composition, said composition comprising (i) a therapeutically effective amount of racemic fexofenadine, (R)-fexofenadine, (S)-fexofenadine, or a pharmaceutically acceptable salt thereof; (ii) a therapeutically effective amount of MK-591, MK-886, or a pharmaceutically acceptable salt thereof.

7. The method of claim 6, wherein the amount of racemic fexofenadine, (R)-fexofenadine, (S)-fexofenadine, or a pharmaceutically acceptable salt thereof, is from 0.01 to 500 mg.

8. The method of claim 6, wherein the amount of the MK-591 or MK-886, or a pharmaceutically acceptable salt thereof, is from 20 mg to 2500 mg.

9. The method of claim 6, wherein optically pure (R)-fexofenadine, or a pharmaceutically acceptable salt thereof, is administered.

10. The method of claim 6, wherein optically pure (S)-fexofenadine, or a pharmaceutically acceptable salt thereof, is administered.

11. A method of treating dermatitis in a human which comprises administering to the human a therapeutically effective amount of optically pure (R)-fexofenadine, optically pure (S)-fexofenadine, or a pharmaceutically acceptable salt thereof, and a therapeutically effective amount of zafirlukast, montelukast, pranlukast, sodium 1-(((R)-(3-(2-(6,7-difluoro-2-quinolinyl)ethynyl)phenyl)-3-(2-(2-hydroxy-2-propyl)phenyl)thio)methyl)cyclopropaneacetate, 1-(((1(R)-(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid, or a pharmaceutically acceptable salt thereof.

12. The method of claim 11, wherein the amount of racemic fexofenadine, (R)-fexofenadine, (S)-fexofenadine, or a pharmaceutically acceptable salt thereof, is from 0.01 to 500 mg.

13. The method of claim 11, wherein the amount of the zafirlukast, montelukast, pranlukast, sodium-1-(((R)-(3-(2-(6,7-difluoro-2-quinolinyl)ethynyl)phenyl)-3-(2-(2-hydroxy-2-propyl)phenyl)thio)methyl)cyclopropaneacetate, or 1-(((1(R)-(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid, or a pharmaceutically acceptable salt thereof, is from 2 mg to 200 mg.

14. The method of claim 11, wherein optically pure (R)-fexofenadine, or a pharmaceutically acceptable salt thereof, is administered.

15. The method of claim 11, wherein optically pure (S)-fexofenadine, or a pharmaceutically acceptable salt thereof, is administered.

* * * * *